(12) United States Patent
Tan et al.

(10) Patent No.: US 8,008,539 B1
(45) Date of Patent: Aug. 30, 2011

(54) GENERATION OF TRANSGENIC HUMAN SOLUBLE AMYLOID PRECURSOR PROTEIN ALPHA EXPRESSING MICE

(75) Inventors: Jun Tan, Tampa, FL (US); William Nikolic, Tampa, FL (US); Huyan Hou, Tampa, FL (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 12/727,679

(22) Filed: Mar. 19, 2010

Related U.S. Application Data

(60) Provisional application No. 61/161,616, filed on Mar. 19, 2009.

(51) Int. Cl.
*A01K 67/00* (2006.01)
*A01K 67/033* (2006.01)
*G01N 33/00* (2006.01)

(52) U.S. Cl. .................................. 800/18; 800/8; 800/3

(58) Field of Classification Search .................... 800/18, 800/8, 3
See application file for complete search history.

(56) References Cited

U.S. PATENT DOCUMENTS

| | | | |
|---|---|---|---|
| 4,736,866 | A | 4/1988 | Leder et al. |
| 5,877,399 | A | 3/1999 | Hsiao et al. |
| 6,175,057 | B1 | 1/2001 | Mucke et al. |
| 6,262,335 | B1 | 7/2001 | Hsiao et al. |
| 6,509,515 | B2 | 1/2003 | Hsiao et al. |
| 7,247,766 | B2 | 7/2007 | Jacobsen et al. |
| 7,432,414 | B2 * | 10/2008 | Chen et al. ............... 800/18 |

OTHER PUBLICATIONS

Aikawa et al. JBC 277(21):18979-18985, 2002.*
Boa et al. Gynogenetic Oncology 84:228-234, 2002.*
Haruyama et al. Curr Protoc Cel Biol. Mar. 2009. Chapter Unit-19. 10. doi:10.1002/0471143030.cb11910s42. pp. 1-12.*
Neurodegenerative printout from http://www.merriam-webster.com/dictionary/neurodegenerative?=show=0&t=128630550. Printout dated Oct. 5, 2010, p. 1.*
Parkinson et al. J Biol Chem 265(21):12602-12610, 1990.*
George et al., APP Intracellular Domain is Increased and Soluble ABeta is Reduced with Diet-Induced Hypercholesterolemia in a Transgenic Mouse Model of Alzheimer Disease, Neurobiology of Disease, 2004, vol. 16, pp. 124-132.
Cachard-Chastel et al., 5-HT4 Receptor Agonists Increase sAPPBeta Levels in the Cortex and Hippocampus of Male C57BL/6j Mice, British Journal of Pharmacology, 2007, vol. 150, pp. 883-892.
Bailey et al., Peripheral Biomarkers in Autism: Secreted Amyloid Precursor Protein-Beta as a Probable Key Player in Early Diagnosis, Int J Clin Exp Med, 2008, vol. 1, pp. 338-344.
Gibbs et al., Pharmaceutical Research in Molecular Oncology, Cell, 1994, vol. 79, pp. 193-198.
Moy et al., Advances in Behavioral Genetics: Mouse Models of Autism, Molecular Psychiatry, 2008, vol. 13, pp. 4-26.
Sokol et. al., High Levels of Alzheimer Beta-Amyloid Precursor Protein (APP) in Children With Severely Autistic Behavior and Aggression, J Child Neurol., 2006, vol. 21, No. 6, pp. 444-449.
Lin et. al., Screening Mixtures by Affinity NMR, J. Org. Chem., 1997, vol. 62, No. 25, pp. 8930-8931.
Fejzo et. al., The Shapes Strategy: an NMR-Based Approach for Lead Generation in Drug Discovery, Chemistry & Biology, 1999, vol. 6, No. 10, pp. 755-769.
Hupp et. al., Small Peptides Activate the Latent Sequence-Specific DNA Binding Function of p53, Cell, 1995, vol. 83, pp. 237-245.
Milner, DNA Damage, p53 and Anticancer Therapies, Nature Medicine, 1995 vol. 1, No. 9, pp. 879-880.

* cited by examiner

*Primary Examiner* — Deborah Crouch
*Assistant Examiner* — Marcia S Noble
(74) *Attorney, Agent, or Firm* — Michele L. Lawson; Smith & Hopen, P.A.

(57) ABSTRACT

The present invention relates to a novel animal model for neurological degenerative diseases, especially autism, relating to overexpression of human secreted APP-alpha. This novel animal model exhibits several aspects of amyloidopathy. The present invention also relates to a method for producing the double transgenic animals, to cells and cell lines derived from these animals. Moreover, a method for the evaluation of the in vivo effects of a test compound on secreted APP-alpha expression and autism pathology in these animals is provided.

2 Claims, 9 Drawing Sheets

GENERATION OF TRANSGENIC HUMAN SOLUBLE AMYLOID PRECURSOR PROTEIN ALPHA EXPRESSING MICE

CROSS REFERENCE TO RELATED APPLICATIONS

This application is a Nonprovisional Application of co-pending U.S. Provisional Application No. 61/161,616 filed Mar. 19, 2009; which application is incorporated herein by reference.

BACKGROUND OF THE INVENTION

First described by Dr. Leo Kanner, autism is a pervasive developmental disorder (PDD) characterized by the presence of limited interests and activities, as well as by impairments in socialization and communication. Despite the fact that there are many suggestions for the causes of this disorder, including, but not limited to, genetics, the environment, and vaccinations, there is no one cause of autism. With the advent of electroencephalography (EEG), observations of aberrant patterns in autistic patients contributed the contemporary understanding of the syndrome as a brain-based disorder. The heterogeneity of the clinical syndrome would seem to indicate that the disorder termed autism may arise from a constellation of different etiologies. For example, about one quarter of autistic patients have comorbid epilepsy. Studies suggest another subgroup, some 40-55% of autistic patients, suffers mental retardation. Furthermore, even though the heritability of autism is relatively high, only some 10% of cases can be attributed to a known genetic aberration.

Although there are diagnostic criteria listed in the Diagnostic and Statistical Manual of Mental Disorders (DSM-IV), the International Statistical Classification of Diseases and Related Health Problems (ICD-10), the Autism Diagnostic Observation Schedule (ADOS) and the Autism Diagnostic Interview-Revised (ADI-R), the disorder is currently diagnosed solely using core behavioral criteria selected to define autism, typically during the toddler or preschool years at the earliest. There is presently no clinical laboratory test for diagnosing autism. To begin intervention at the earliest possible time, the development of biological quantitative methods to predict the presence or risk of autism is necessary.

Proteolytic cleavage of amyloid precursor protein (APP) by the sequential actions of β- and γ-secretases form the neurotoxic amyloid beta (Aβ) peptide, which typically consists of 40 or 42 amino acid residues (the amyloidogenic pathway). On the other hand the non-amyloidogenic pathway consists of APP cleavage by α-secretase which yields the neurotrophic product, secreted APP-α (sAPP-α). As α-secretase cleaves APP within the Aβ sequence, Aβ formation is subsequently prevented. In a recent report Sokol and colleagues demonstrated, in children with severe autism and aggressive behavior, that serum sAPP-α levels were more than twice that of children without autism and up to four times higher than observed in children with mild autism [see Sokol D K, Chen D, Farlow M R et al. High levels of Alzheimer beta-amyloid precursor protein (APP) in children with severely autistic behavior and aggression. J Child Neurol. 2006; 21(6): 444-9).

Based on the Sokol study, the inventors speculated that sAPP-α is a peripheral biomarker that can be used for the diagnosis of autism. In addition, they developed a sensitive enzyme-linked immunosorbent assay (ELISA) to specifically measure sAPP-α secretion in human plasma and umbilical cord blood and they hypothesize that this ELISA will show a significant difference in sAPP-α levels of autistic patients when compared to healthy individuals. The goal was to design a laboratory tool for early diagnosis of autism. (see Bailey et al. Peripheral biomarkers in Autism: secreted amyloid precursor protein-α as a probable key player in early diagnosis. Int J Clin Exp Med (2008) 1, 338-344).

There are substantial gaps, however, in the knowledge of the neurodevelopmental mechanisms underlying autism which arise largely from the difficulty of characterizing the circuitry subserving higher mental functions, the complexity of the genetic underpinnings of "normal" versus "abnormal" behavioral variation in childhood. Moreover, there is a lack of satisfactory autism animal models. (see Moy S S, Nadler J J. Advances in behavioral genetics: mouse models of autism. Mol Psychiatry. 2008; 13(1): 4-26)). What is needed, therefore, is an experimental animal model which expresses a peripheral biomarker to test target diagnostic and therapeutic agents for autism.

SUMMARY OF INVENTION

The present invention features non-human transgenic animal models for neurodegenerative disorders, such as autism, wherein the transgenic animal is characterized by overexpression secreted amyloi precursor protein alpha (sAPP-alpha) gene product. The transgenic animals may be either homozygous or heterozygous for the alteration. Bigenic animals are further characterized by development of autism-associated pathology as verified quantitatively and qualitatively.

In another aspect the invention features a method of screening for biologically active agents that modulate phenomena associated with autism, wherein the method involves the steps of combining a candidate agent with a non-human animal transgenic for sAPP-alpha gene product, and determining the effect of said agent upon a phenomenon associated with autism.

A primary object of the invention is to provide a transgenic animal model for examining the effects of a candidate agent (e.g., a small molecule drug or an endogenous factor) on a phenomenon associated with autism. Such transgenic animal models are useful for screening candidate agents for use in treating or relieving the symptoms of autism. Another object is to provide an animal model for autism pathologies, thereby providing a means to study these conditions.

An advantage of the claimed invention is that the transgenic animal models described and claimed herein exhibit phenomena associated with autism pathologies (e.g. overexpression of sAPP-alpha). Moreover, the transgenic animal models of the invention develop autism-associated pathology more quickly than do conventional transgenic animal models.

These and other objects, advantages and features of the present invention will become apparent to those persons skilled in the art upon reading the details of the invention more fully set forth below.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

As stated above, there is no current molecular marker or laboratory tool capable of diagnosing autism at an early age. Studies have identified high sAPP-alpha levels in autistic patients yet no further studies have been performed due to a lack on animal models that express this molecule. Here, the inventors have generated transgenic mice that overexpress sAPP-alpha molecule in their brains. These mice show behavioral and social Impairment that is typically seen among autism-like disorders. Furthermore, histology revealed irregular neural networks which need to be further identified. Overall, this invention opens a new avenue into studying sAPP-alpha role not just in autism but in neurodevelopment in general.

Therefore, in one embodiment, the invention includes a transgenic human soluble amyloid precursor (sAPP-alpha) murine model. This embodiment encompasses metabolite of APP with an obvious signal for phosphor tau protein. Applications of the murine model include studies and therapy development for: neuro-development; neuro-degeneration; neuro-protection; neuro-differentiation; neuro-inflammation; neuronal formation, stabilization, reorganization; microtubles and microfilament formation, stabilization, reorganization; neurofilibrilary tangles (nfts); and various neuro-degenerative disorders such as Asperger's disease, autism spectrum disorder, tauopathies (frontotemporal dementia, pick's disease, supranuclear palsy, corticobasal degeneration, and frontotemporal dementia with parkinsonism linked to chromosome 17) and Alzheimer's disease.

The potential application and benefits of this discovery are profound, since transgenic animals provide tools and plausible markers for the diagnosis of autism as well as providing a better understanding of neurodevelopment.

Secreted APP-α (sAPP-α) as a Biomarker for Autism.

Figure 1:
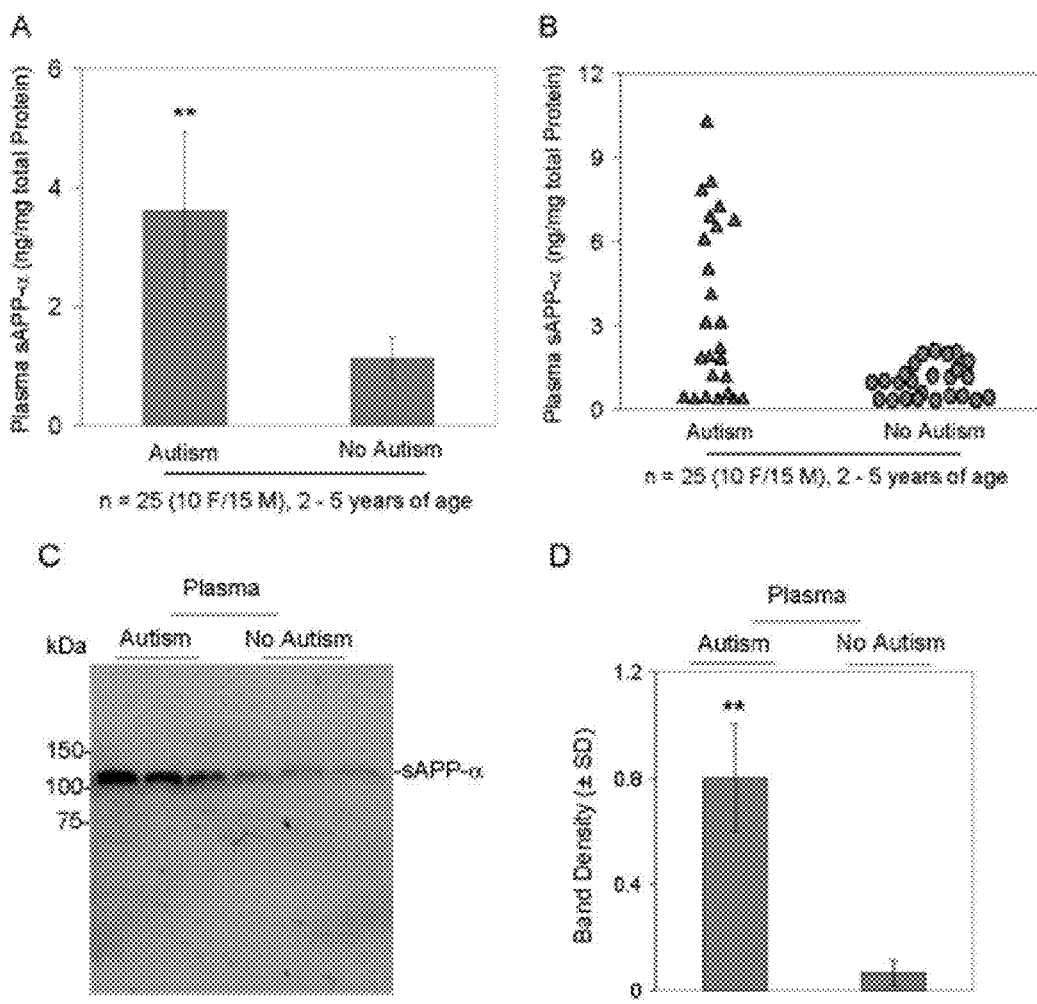
FIG. 1. Levels of sAPP-α are elevated in autistic children. (A and B) Plasma sAPP-α levels were measured by sAPP-α ELISA. Data are presented as mean±SEM (n=25 for autistic children, 15 ♂/10 ♀F; n=25 for healthy age matched children, 15 ♂/10 ♀) of sAPP-α (ng/mg total plasma protein). (C) Western blotting analysis consistently shows increased sAPP-α levels in autistic children versus age-matched healthy controls as indicated. Blood plasma samples for both groups of children were randomly selected. The selected samples were then pooled and loaded in triplicate for electrophoresis. The lack of similarity between all three lanes for the autism samples is not due to differences in the individual samples. (D) As quantified in comparison to total protein (normalization), densitometry analysis shows significantly increased density in Western blotting band density as indicated. Data are presented as mean±SEM [n=15 (autistic children), 11 ♂/4 ♀; n=15 (healthy controls), 8 ♂/7 ♀] of Western blotting band density.

The inventors have recently developed a sensitive ELISA to specifically measure sAPP-α secretion in plasma. In order to validate this assay, the inventors measured plasma sAPP-α levels in autistic and age-matched control blood samples using the inventor's novel sAPP-α ELISA and found a significantly increased level of sAPP-α in 60% of the known autistic children, compared to healthy age-matched children (FIGS. 1A and B, P<0.05). Post hoc analysis revealed no association between the severity of aggression, social, or communication sub-scores (Revised Autism Diagnostic Instrument; ADI-R) and elevations in sAPP-α (P>0.05). Such findings point to a group of autistic patients which could be identified in early childhood by levels of sAPP-α. As an additional confirmatory measure, the inventors performed Western blot analysis on these samples. As shown in FIGS. 1C, D, Western blot analysis consistently showed increased sAPP-α levels in autistic children versus age-matched healthy controls.

Figure 2:
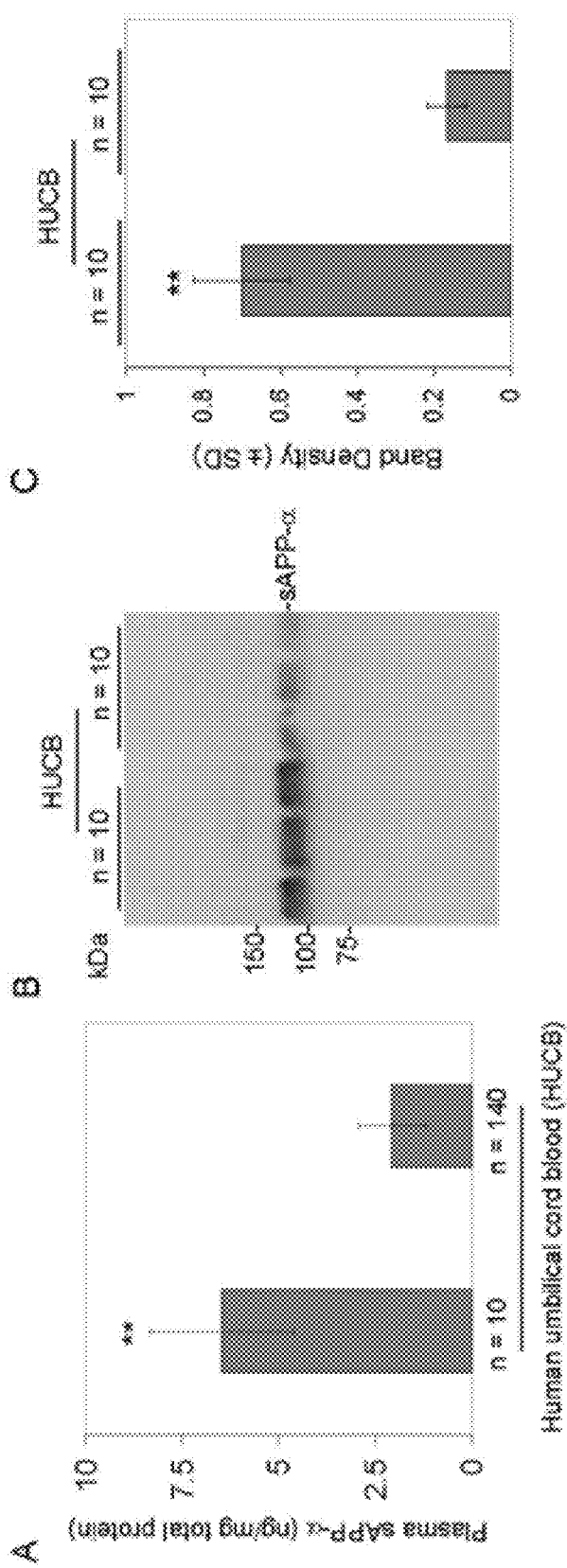
FIG. 2. A significantly increased level of sAPP-α is observed in approximately 7% of 150 human umbilical cord blood (HUCB) samples. (A) The plasma was isolated, prepared, and subjected to sAPP-α ELISA. Data indicated elevated levels (>3 ng/mg total plasma protein) of plasma sAPP-α in 10 of 150 samples. Data are presented as mean±SEM of sAPP-α (ng/mg total protein). (B) Western blotting analysis demonstrated increased sAPP-α levels in the same samples which demonstrated elevated sAPP-α by ELISA. (C) As quantified with total protein (normalization), densitometry analysis shows significantly increased density of Western blotting band as indicated. Likewise, samples demonstrating a <3 ng/mg difference in sAPP-α by ELISA demonstrated the same changes upon Western blotting analysis. HUCB samples from both groups of infants were randomly selected. The selected samples were then pooled and loaded in triplicate for electrophoresis. Data are presented as mean±SEM (n=10, 8 M/7 F) of band density.

In order to further evaluate the inventor's optimized sAPP-α ELISA, the inventors acquired 150 human umbilical cord blood samples from Saneron CCEL Therapeutics, Inc. (Tampa, Fla.). These HUCB samples were screened and found to be free of infectious diseases. The plasma was isolated, prepared, and subjected to sAPP-α ELISA. Data indicated significantly elevated levels (>3 ng/mg total plasma protein) of plasma sAPP-α in 10 of 150 samples (FIG. 2A). To confirm the ELISA results, the inventors performed Western blot analysis on 20 samples from the original pool of 150. Ten of these plasma samples had concentrations sAPP-α greater than or equal to 3 ng per mg of total protein by ELISA while the other 10 samples had less than 3 ng of sAPP-α per mg of total protein. Consistent with the inventor's ELISA data (FIG. 2B, C), Western blot analysis demonstrated increased sAPP-α levels in the same 10 samples originally identified as "elevated" by the inventor's ELISA. Likewise, samples demonstrating less than 3 ng of sAPP-α per mg of total plasma protein by ELISA demonstrated the same changes upon Western blot analysis (FIG. 2C). These results indicate that significant differences in levels of sAPP-α production can be measured at birth using the inventor's ELISA.

The goal of this study was to explore the plausible use of peripheral biomarkers in the early diagnosis of autism via a sensitive ELISA. Taking into account previous studies showing that brain-derived neurotrophic growth factor (BDNF) is associated with macrocephaly in autistic patients, the inventors considered BDNF a likely biomarker candidate for the inventor's study. After further literature search, the inventors discovered that not only is BDNF unreliable, but it is also not mutually exclusive to autism patients and so it would not make an effective biomarker for diagnostic purposes. The discovery of elevated levels of secreted amyloid precursor protein alpha (sAPP-α) in children with autism by Sokol and colleagues led to the inventor's speculation that sAPP-α could be used as a diagnostic biomarker.

This was only the second investigation which has uncovered elevated sAPP-α in autistic patients. The inventor's preliminary results suggest a possible biomarker for affected individuals. The potential implications of these findings in the context of the known neurotrophic properties of sAPP-α, the observed brain overgrowth in certain brain regions of children with autism, and the lack of cerebral plaques found on histological examination of brains of autistic individuals are quite significant. Although sAPP-α has not yet been shown to be directly pathogenic, as a plasma biomarker, it may help delineate a subset of children in which early regional brain overgrowth is necessary and sufficient for the development of autism and may even represent a mechanism by which overgrowth may occur. Indeed it has previously been shown that sAPP-α, is able to potentiate nerve growth factor (NGF)/ retinoic acid (RA)-induced transdifferentiation of bone marrow-derived adult progenitor cells (MAPCs) into neural progenitor cells and, more specifically, augments their differentiation into a cholinergic-like neuronal phenotype. Interestingly, cholinergic hypertrophy is a common feature of autism.

In addition to using the inventor's ELISA to measure sAPP-α levels in serum, the inventors sought to test its ability to measure sAPP-α levels in human umbilical cord blood, thereby examining the possible use of the ELISA for such measurements at birth. A significant elevation in sAPP-α levels in 7% of the inventor's samples confirm that sAPP-α can indeed be identified in HUCB via the inventor's ELISA. It has previously been shown by in vitro methods that BDNF confers a 1.7-fold increase in sAPP-α secreted from neuron-like cells, and in light of the inventor's findings of a high incidence (7%) of significantly elevated sAPP-α in HUCB samples, relative to the incidence of autism in the general population, the inventors can not rule-out that elevations in sAPP-α do not represent a normal or non-autistic variant of perinatal development. Furthermore, a subset of these 7% of HUCB samples may actually represent a group of children in which sAPP-α remains elevated into childhood and potentially leads to abnormal brain development. This hypothesis, and whether children with other conditions such as mental retardation and Down syndrome may also express comparably high plasma levels of sAPP-α, remains to be elucidated.

Transgenic Mouse Model for Autism.

Currently autism is diagnosed solely using core behavioral criteria selected to define autism, typically during the toddler or preschool years at the earliest. Such a method of evaluation often limits the age at which reliable diagnoses can be made to the periods after five years of age, when behavior-based diagnostic distinctions and long-term outcome are more reliable and predictable. To begin intervention at the earliest possible time, the development of biological quantitative methods to predict the presence or risk of autism is necessary. Recent study found increased alpha-secretase activity and associated sAPP-alpha in autistic patients. Because sAPP-alpha is neurotrophic and important in early brain development it is important to fully characterize this protein and determine its role in brain development.

There is currently no single molecular marker or laboratory tool capable of diagnosing autism at an early age. This invention will help the study one such molecule that has been identified in autism and provide us better understanding of its role in neural development by studying its function in these transgenic sAPP-alpha over-expressing mice.

No study has reported a use or generation of transgenic animals that overexpress sAPP-alpha in their brain. To elucidate the effects of sAPP-alpha of brain development the inventors generated sAPP-alpha transgenic animals.

The transgenic non-human animals of the present invention are preferably mammals. More preferably, the animals are rodents. Most preferably, the animals are mice. The present invention also relates to descendants of the transgenic non-human animals, obtained by breeding with the same or with another phenotype. The present invention further provides a cell line or primary cell culture as well as an organotypic brain slice culture derived from the transgenic non-human animal or its descendants.

Another embodiment of the invention includes the use of the transgenic non-human animal or a cell line or an organotypic brain slice culture as a model for neurodegenerative disease, especially as a model for autism.

Specifically, the transgenic non-human animal, or animal cells derived thereof, can be used to investigate the pathological course of autism and to screen for compounds preventing or altering the pathological course of autism as measured, for example, by their effect on the amount of APP cleavage products, neuropathology and behavioral alterations.

The present invention further includes a method of producing a transgenic non-human animal whose genome incorporates DNA comprising a coding sequence which encodes the human sAPP-alpha operably linked to a regulatory promoter sequence.

Transgenic mice are achieved routinely in the art using the technique of microinjection, as described in U.S. Pat. No. 4,736,866 issued to Leder et al., U.S. Pat. No. 7,247,766 to Jacobsen et al., and as provided by B. Hogan et al. entitled "Manipulating the Mouse Embryo: A Laboratory Manual", Ed. 2, pp. 89 204. Plainview, N.Y.: Cold Spring Harbor Laboratory, USA (1995). Further methods for the production of a transgenic non-human animal, for example a transgenic mouse, comprise introduction of a targeting vector into a germ cell, an embryonic cell, stem cell or an egg or a cell derived there from.

For these studies, the constructs are introduced into animal embryos using standard techniques such as microinjection or embryonic stem cells. Cell culture based models can also be prepared by two methods. Cell cultures can be isolated from the transgenic animals or prepared from established cell cultures using the same constructs with standard cell transfection techniques.

The method for producing transgenic non-human animals whose genome incorporates DNA comprising a coding sequence which encodes the human sAPP-alpha operably linked to a regulatory promoter sequence comprises:

(a) introducing a DNA construct comprising a coding sequence which encodes human beta-secretase and a regulatory sequence which is operably linked to the coding sequence into a cell or embryo;
(b) introducing a DNA construct comprising a coding sequence which encodes human APP London and a regulatory sequence which is operably linked to the coding sequence into a cell or embryo;
(c) generating a transgenic animal from each of the said cells or embryos; and
(d) crossbreeding the said transgenic animals.

In yet another embodiment, a method for testing the efficacy of a treatment for a degenerative brain condition associated with an overexpression of sAPP-alpha comprising exposing a transgenic animal to that treatment and determining the effect of the treatment on the amount and the localization of APP cleavage products, neuropathology and behavioral alterations is provided.

As used herein, "test compound" is intended to mean any compound which is being screened for preventing, inhibiting or reversing degenerative brain condition e.g. autism using the transgenic animals as well as organotypic brain slice cultures or cells derived thereof described herein. It is also understood that a "test compound", which is active in preventing, inhibiting or reversing autism, can subsequently be used in pharmaceutical compositions for the treatment of degenerative brain conditions involving sAPP-alpha production, preferably for the treatment of autism.

The compounds which can be tested and identified according to a method of the invention may be expression libraries, e.g., cDNA expression libraries, peptides, proteins, nucleic acids, antibodies, small organic compounds, hormones, peptidomimetics, PNAs or the like (Milner J. DNA damage, p53 and anticancer therapies. Nat Med. 1995. 1:879 880; Hupp T R. Small peptides activate the latent sequence-specific DNA binding function of p53. Cell. 1995.83:237 245; Gibbs J B, Oliff A. Pharmaceutical research in molecular oncology. Cell. 1994 Oct. 21; 79(2): 193 8.).

The compounds isolated by the above methods can also serve as lead compounds for the development of analog compounds. Identification of analog compounds can be performed through use of techniques such as self-consistent field (SCF) analysis, configuration interaction (CI) analysis, and normal mode dynamics analysis. Computer programs for implementing these techniques are available; e.g., Rein, Computer-Assisted Modeling of Receptor-Ligand Interactions (Alan Liss, New York, 1989). Methods for the preparation of chemical derivatives and analogues are well known to those skilled in the art and are described in, for example, Beilstein, Handbook of Organic Chemistry, Springer edition New York Inc., 175 Fifth Avenue, New York, N.Y. 10010 U.S.A. and Organic Synthesis, Wiley, New York, USA. Furthermore, said derivatives and analogues can be tested for their effects according to methods known in the art; see also supra. Furthermore, peptidomimetics and/or computer aided design of appropriate derivatives and analogues can be used, for example, according to the methods described above. Methods for the lead generation in drug discovery also include using proteins and detection methods such as mass spectrometry (Cheng et al. J. Am. Chem. Soc. 1995. 117:8859 60) and some nuclear magnetic resonance (NMR) methods (Fejzo et al., Chem. Biol. 1999. 6:755 69; Lin et al., J. Org. Chem. 1997. 62:8930 8931).

In a further embodiment, the invention provides a pharmaceutical composition comprising a test compound identified by the screening method of the present invention and a pharmaceutically acceptable carrier. The present invention further provides a pharmaceutical composition comprising a test compound identified by a screening method of the present invention for use in the treatment of neurodegenerative conditions including autism and a pharmaceutically acceptable carrier.

In accordance with this, the present invention also relates to a method of producing a drug comprising the steps of (1) synthesizing the test compound identified as useful in the treatment of a neurodegenerative condition or an analog or derivative thereof in an amount sufficient to provide said drug in a therapeutically effective amount to a subject; and/or (2) combining the test compound identified as useful in the treatment of a neurodegenerative condition or an analog or derivative thereof with a pharmaceutically acceptable carrier.

Example I

Generation of Transgenic Animal Models

Secreted APP-alpha cDNA encoding pcDNA3.1 (+/−) vector was digested with EcoRI and HinDIII restriction endonucleases (RE) and then ends were blunted. Simultaneously, JHU-2 vector that is carrying prion protein promoter (mainly expressed in the brain) was digested with XhoI RE and blunted. These two species were allowed to ligate and later transformed into DH5alpha competent cells. Colonies were selected and digested with NarI and XbaI RE to confirm orientation. Once, correct colonies were identified, a Maxiprep (Quiagen) was used to amplify these species that were microinjected into B57BlJ6 embryos by the H. Lee Moffitt Cancer Center Animal Core Facility. Generated littermates demonstrate impaired social and behavioral interactions similar to autism-like disorders and histology reveals irregular neural networks.

Figure 3:
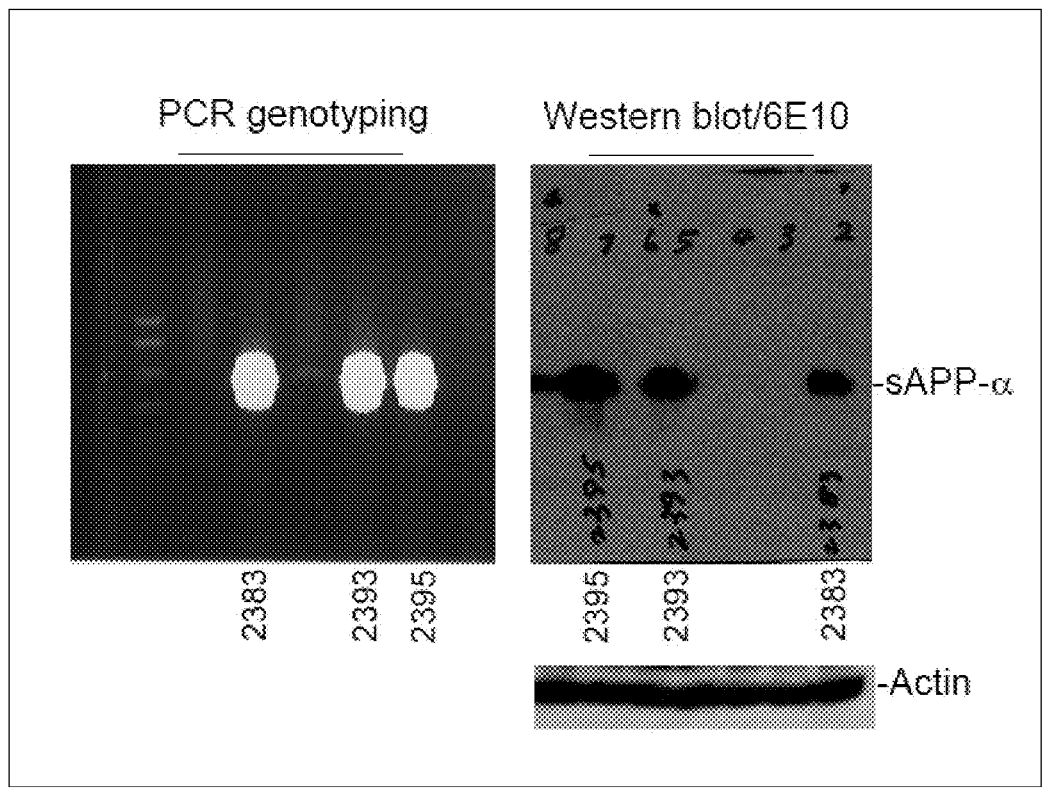
FIG. 3: (LEFT) depicts genotyping of these animals (2383, 2393, 2395 indicate different mice ID's) through PCR analysis. (RIGHT) Western blot analysis for above mentioned samples. Membrane was probed for 6ElO antibody that recognize 1-17 portion of amyloid beta peptide and is positive for sAPP-alpha. Actin expression is also shown at the bottom as an internal control to demonstrate equal protein loading for each sample.

FIG. 3 depicts genotyping of these animals (2383, 2393, 2395 indicate different mice ID's) through PCR analysis. Western blot analysis for above mentioned samples are also shown, wherein membranes were probed for 6E10 antibody that recognize 1-17 portion of amyloid beta peptide and is positive for sAPP-alpha. Actin expression is also shown at the bottom as an internal control to demonstrate equal protein loading for each sample.

Figure 4:
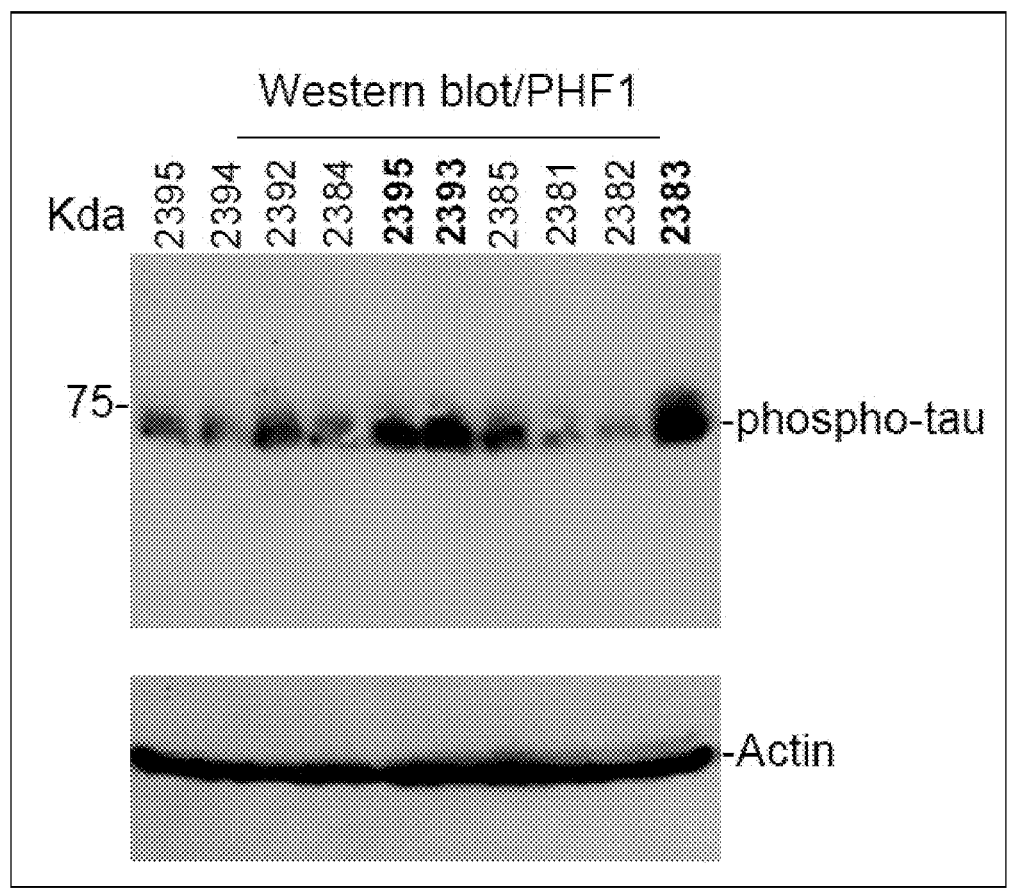
FIG. 4: Samples were ran on a western blot and probed for paired helical filaments (PHF). As indicated samples 2383, 2393, and 2395 that are positive for sAPP-alpha are also positive for PHF as indicated following probing with PHF1 antibodies. Actin was used as internal control to demonstrate equal loading for all samples.

Referring to FIG. 4, samples were ran on a western blot and probed for paired helical filaments (PHF). As indicated samples 2383, 2393, and 2395 that are positive for sAPP-alpha are also positive for PHF as indicated following probing with PHF1 antibodies. Actin was used as internal control to demonstrate equal loading for all samples.

Figure 5:
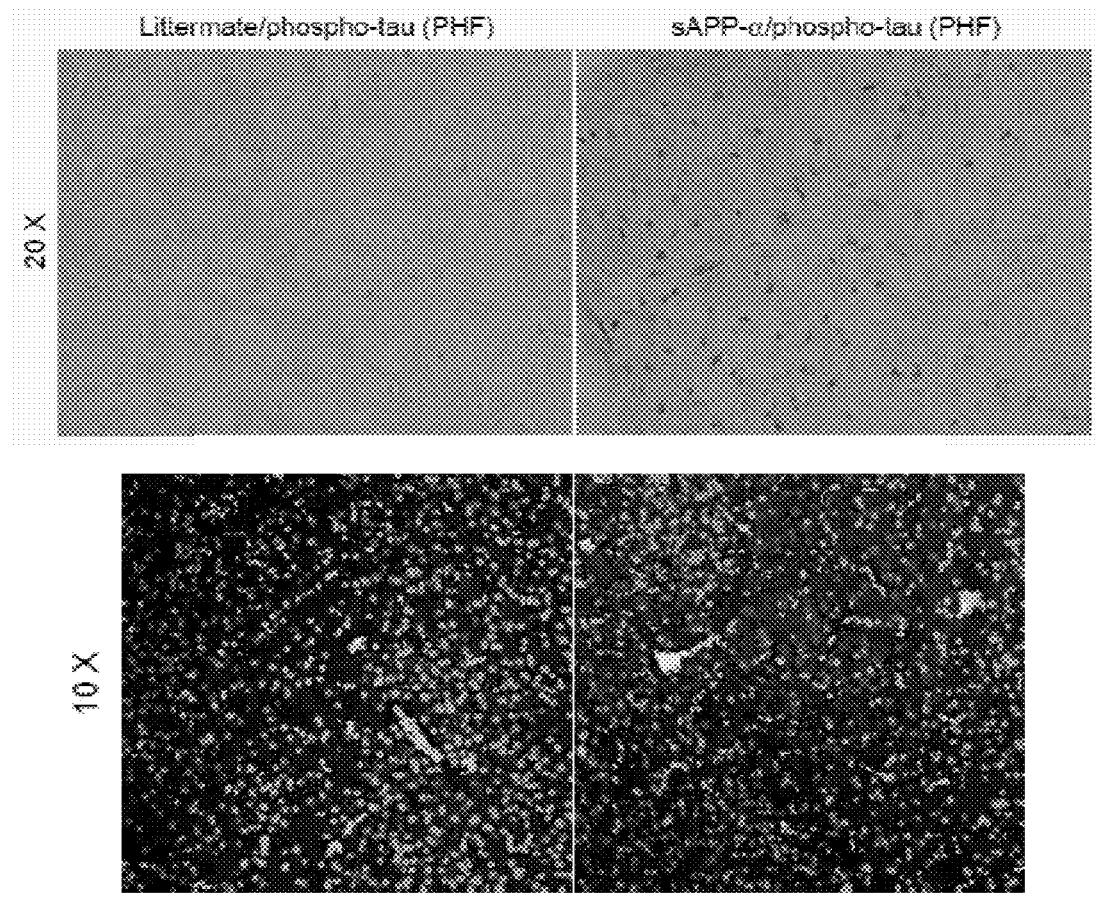
FIG. 5: Immunohistochemical staining was performed on Tg sAPP-alpha positive brain sections versus littermates controls. Top panels indicate positive staining for phospho-tau in Tg sAPP-alpha littermates (right) versus age-matched wild type littermates (left). Bottom panels indicate phospho-tau staining following immuno-fluorescent staining for PHF1. Once again panel on the right represents Tg sAPP-alpha animals and the one on the left age-matched wild type littermates.

Immunohistochemical staining was performed on Tg sAPP-alpha positive brain sections versus littermates controls (FIG. 5). Top panels indicate positive staining for phospho-tau in Tg sAPP-alpha littermates (right) versus age-matched wild type littermates (left). Bottom panels indicate phospho-tau staining following immuno-fluorescent staining for PHF1. Once again panel on the right represents Tg sAPP-alpha animals and the one on the left age-matched wild type littermates.

Example II

Behavioral Testing of Transgenic Animals

Figure 6:
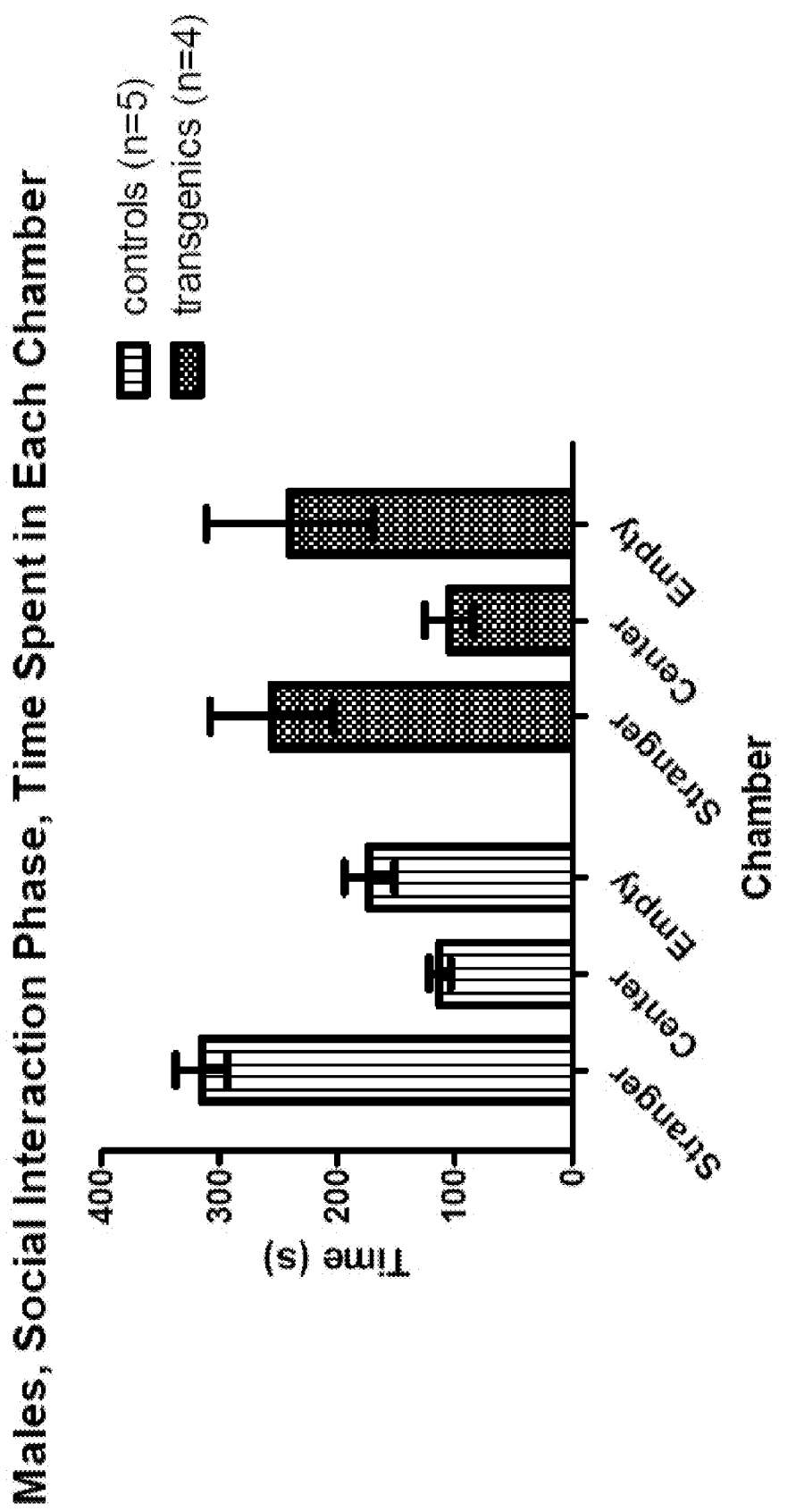
FIG. 6: sAPPα transgenic mice spend equal time in isolation and with an unfamiliar mouse compared to controls who spend more time with a stranger than by itself. Mice were placed in a three-chambered apparatus, for 10 minutes, that provided a test mouse with the option of socializing with a strange mouse or isolation.

As shown in FIG. 6, sAPP-alpha transgenic mice spend equal time in isolation and with an unfamiliar mouse compared to controls who spend more time with a stranger than by itself. Mice were placed in a three-chambered apparatus, for 10 minutes, that provided a test mouse with the option of socializing with a strange mouse or isolation. These results show that transgenics exhibit no preference for social interaction with an unfamiliar mouse compared to controls and suggest impaired sociability in sAPPα transgenic mice.

Figure 7:
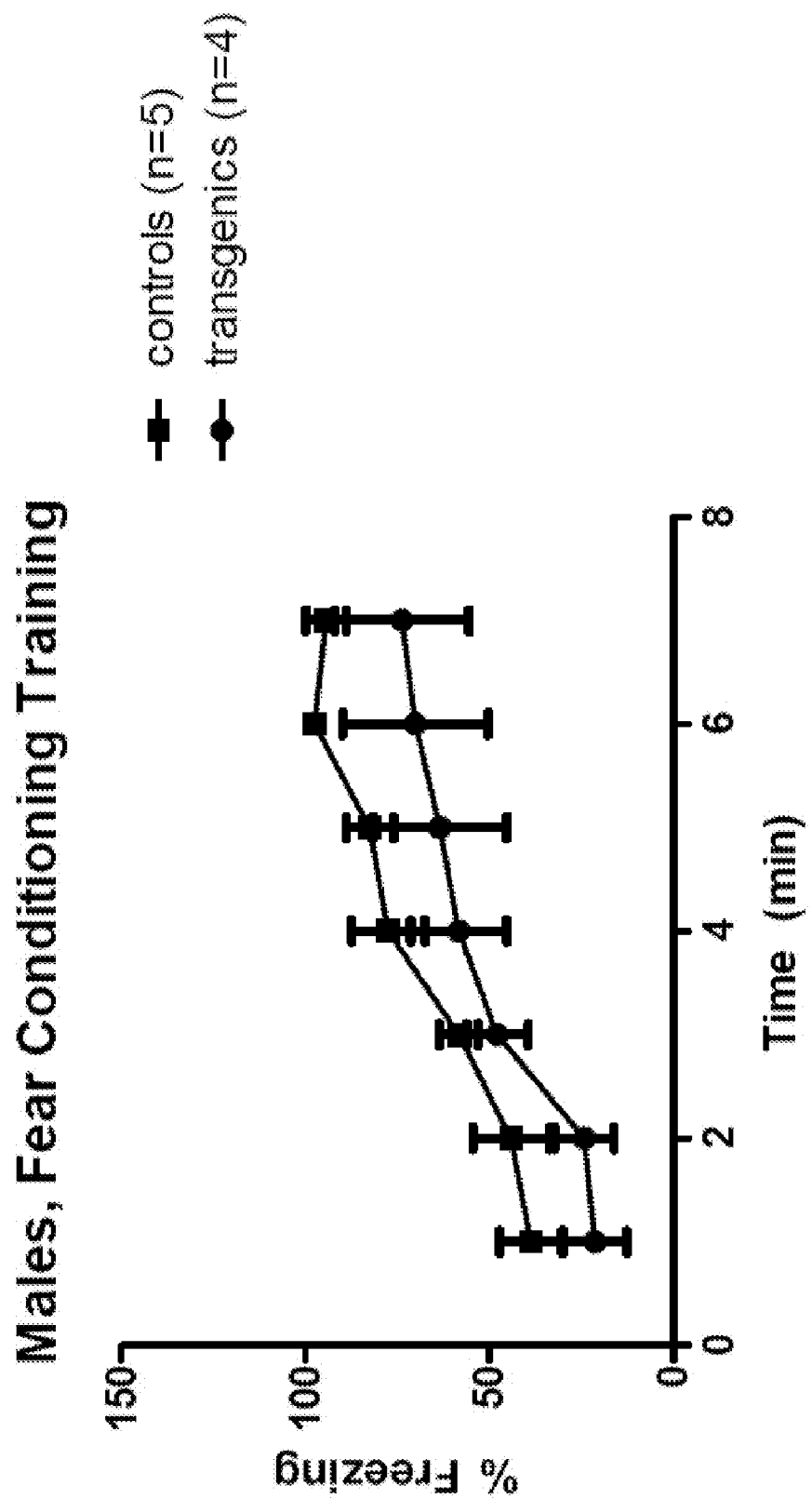
FIG. 7: sAPPα mice have a similar learning ability to controls but exhibit less percentage freezing. Mice were trained to associate a 30-second 80 dB tone with a 2-second 0.5 mA footshock.
Figure 8:
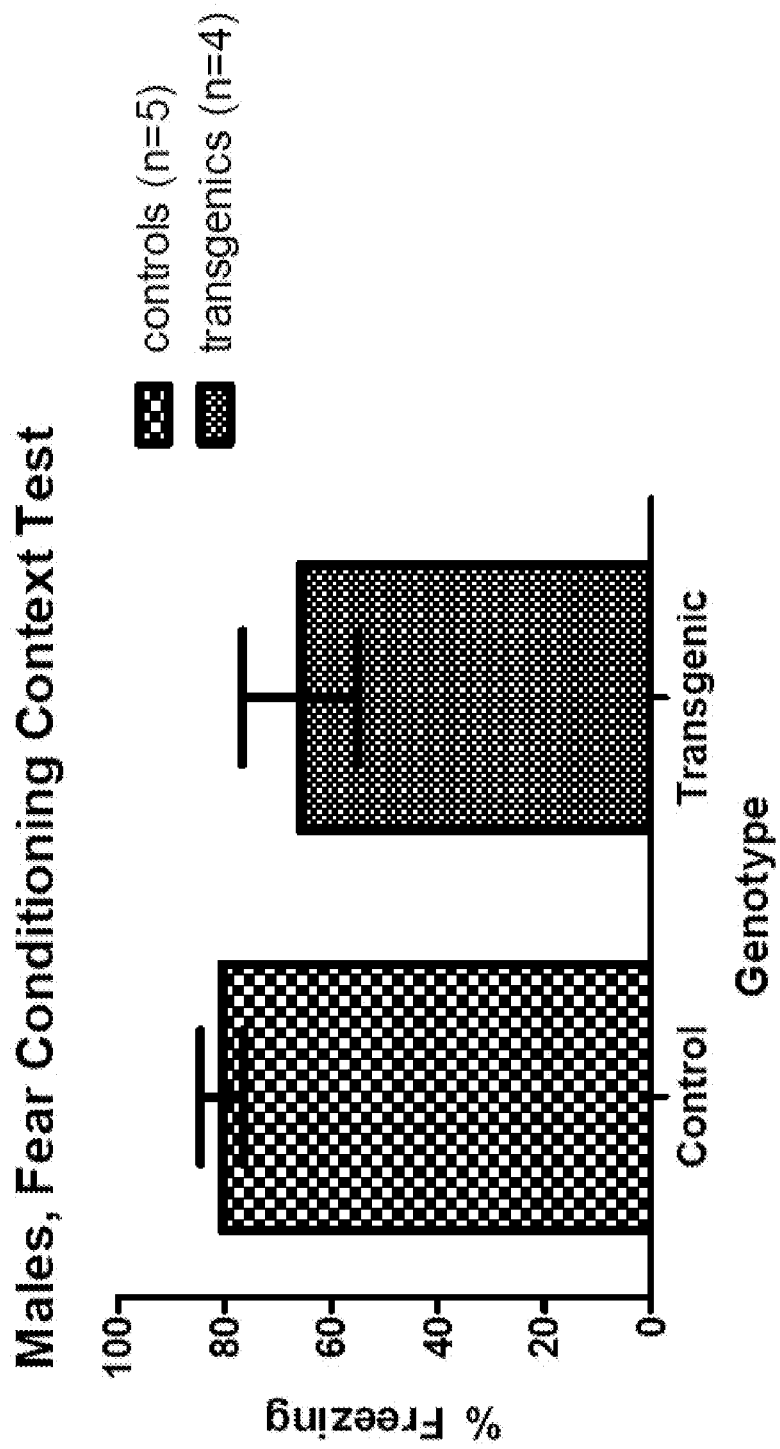
FIG. 8: Both transgenic mice and controls exhibit hippocampal-dependent learning. Mice were placed in training environment 24 hours later for 3 minutes. This suggests that there is no cognitive deficit in the transgenic mice compared to controls.

Referring now to FIG. 7; sAPPα mice have a similar learning ability to controls but exhibit less percentage freezing. Mice were trained to associate a 30-second 80 dB tone with a 2-second 0.5 mA footshock. Both transgenic mice and controls exhibit hippocampal-dependent learning. Mice were placed in training environment 24 hours later for 3 minutes. This suggests that there is no cognitive deficit in the transgenic mice compared to controls (FIG. 8).

Figure 9:
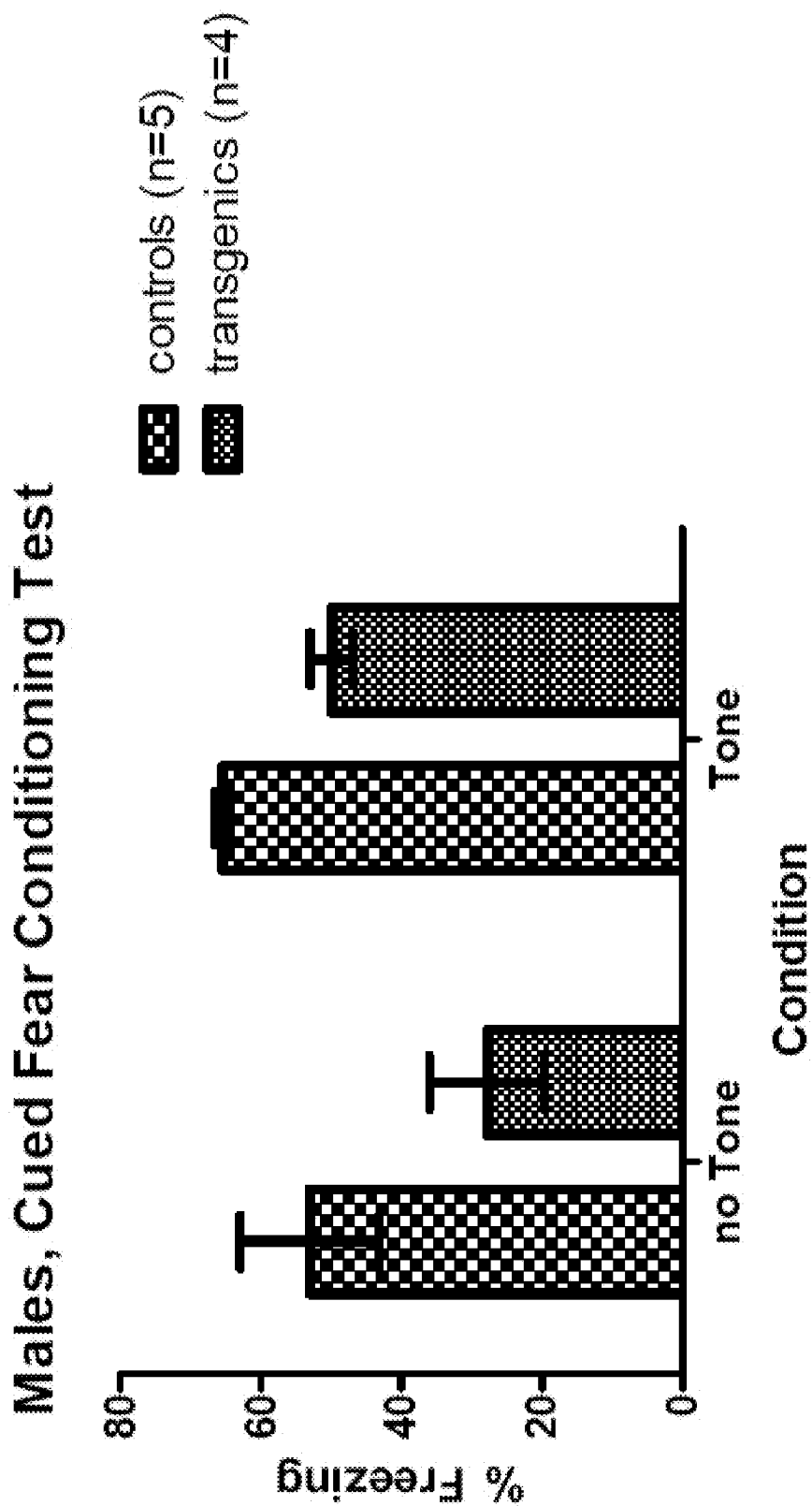
FIG. 9: Both transgenic and control mice show amygdala-dependent learning, however transgenic mice freeze less than controls. Mice were placed in a novel environment for 3 minutes and exposed to the tone they heard during training. This confirms the cognitive ability of the transgenic mice but implies fearlessness compared to control mice which may mean that sAPPα may affect the amygdala and cause a reduction in fear response.

Both transgenic and control mice show amygdala-dependent learning, however transgenic mice freeze less than controls (FIG. 9). Mice were placed in a novel environment for 3 minutes and exposed to the tone they heard during training. This confirms the cognitive ability of the transgenic mice but implies fearlessness compared to control mice which may mean that sAPPα may affect the amygdala and cause a reduction in fear response.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense. All materials cited are incorporated by reference as though fully contained herein.

It is also to be understood that the following claims are intended to cover all of the generic and specific features of the invention herein described, and all statements of the scope of the invention which, as a matter of language, might be said to fall therebetween. Now that the invention has been described,

What is claimed is:

1. A transgenic mouse or progeny thereof whose genome comprises a transgene, said transgene having a nucleic acid encoding a secreted soluble human amyloid precursor protein alpha (sAPP-alpha) operably linked to a promoter capable of driving expression of a gene in the brain, wherein said transgenic mouse overexpresses sAPP-alpha in its brain, wherein said transgenic mouse is homozygous for said transgene, and wherein said transgenic mouse develops at least one symptom associated with autism.

2. A method of testing the efficacy of a candidate compound for the treatment of autism, comprising:
   administering a compound to said transgenic mouse of claim 1; and
   comparing said transgenic mouse administered said compound to a transgenic mouse of claim 1 not administered said compound to determine if said compound alleviates a symptom associated with autism;
   wherein said compound is identified as a candidate compound that is potentially effective for the treatment of autism if said compound alleviates at least one symptom of autism.

* * * * *